(12) United States Patent
Stayshich et al.

(10) Patent No.: US 11,629,151 B2
(45) Date of Patent: Apr. 18, 2023

(54) METHOD FOR PREPARING INDOLENAPHTHOPYRANS

(71) Applicant: Transitions Optical, Ltd., Tuam (IE)

(72) Inventors: Ryan Stayshich, Pittsburgh, PA (US); Robert W. Walters, Murrysville, PA (US)

(73) Assignee: Transitions Optical, Ltd., Tuam (IE)

( * ) Notice: Subject to any disclaimer, the term of this patent is extended or adjusted under 35 U.S.C. 154(b) by 0 days.

(21) Appl. No.: 17/416,079

(22) PCT Filed: Dec. 21, 2018

(86) PCT No.: PCT/EP2018/086597
§ 371 (c)(1),
(2) Date: Jun. 18, 2021

(87) PCT Pub. No.: WO2020/126033
PCT Pub. Date: Jun. 25, 2020

(65) Prior Publication Data
US 2022/0073533 A1    Mar. 10, 2022

(51) Int. Cl.
*C07D 491/052*    (2006.01)
*C07D 209/80*    (2006.01)
*C07D 213/81*    (2006.01)

(52) U.S. Cl.
CPC ....... *C07D 491/052* (2013.01); *C07D 209/80* (2013.01); *C07D 213/81* (2013.01)

(58) Field of Classification Search
CPC . C07D 213/81; C07D 491/052; C07D 209/80
See application file for complete search history.

(56) References Cited

U.S. PATENT DOCUMENTS

| | | | |
|---|---|---|---|
| 5,645,767 A | 7/1997 | Van Gemert | |
| 6,113,814 A | 9/2000 | Gemert et al. | |
| 6,555,028 B2 | 4/2003 | Walters et al. | |
| 9,028,728 B2 | 5/2015 | Bancroft et al. | |

FOREIGN PATENT DOCUMENTS

WO    9923071 A1    5/1999

OTHER PUBLICATIONS

Brunner et al., Enantioselective Catalyses; 126: Axially Chiral N,N-Ligands with Binaphthyl/Bipyridyl Structure, Synthesis, 1999, No. 3, pp. 429-434.*

Cho et al., "Intramolecular Oxidative C—N Bond Formation for the Synthesis of Carbazoles: Comparison of Reactivity between the Copper-Catalyzed and Metal-Free Conditions", Journal of the American Chemical Society, 2011, pp. 5996-6005, vol. 133:15.

Rozovsky et al., "Synthesis of Antitumor Carbazole-Amonafide Structural Hybrids", European Journal of Organic Chemistry, 2015, pp. 1811-1818, vol. 2015:8.

* cited by examiner

*Primary Examiner* — Deepak R Rao
(74) *Attorney, Agent, or Firm* — The Webb Law Firm

(57) ABSTRACT

Provided is a synthetic intermediate for the preparation of photochromic indolenaphthopyran compounds having the core skeletal structure of Formula (I): wherein m is 0 to 4, n is 0 to 4, $R^1$ and $R^2$ are each independently hydroxyl, cyano, (meth)acrylate, amino, halo, substituted or unsubstituted alkyl, boronic ester, boronic acid, polyether, polyester, polycarbonate, polyurethane, substituted or unsubstituted aryl, substituted or unsubstituted heterocycloaryl, substituted or unsubstituted heteroaryl, substituted or unsubstituted alkoxy, substituted or unsubstituted aryloxy, substituted or unsubstituted alkylthio, substituted or unsubstituted arylthio, ketone, aldehyde, ester, carboxylic acid, carboxylate, amide, carbonate, carbamate, urea, siloxane, alkoxysilane, or polysiloxane; $R^3$ is substituted or unsubstituted 2-pyridyl or substituted or unsubstituted 2-quinolyl; and $R^4$ is hydrogen, substituted or unsubstituted alkyl, alkoxymethyl, substituted or unsubstituted silyl, or acyl. Also provided is a process for producing an indolenaphthol compound which includes cyclizing the phenylnaphthol compound of Formula (I) in the presence of a catalyst.

Formula (I)

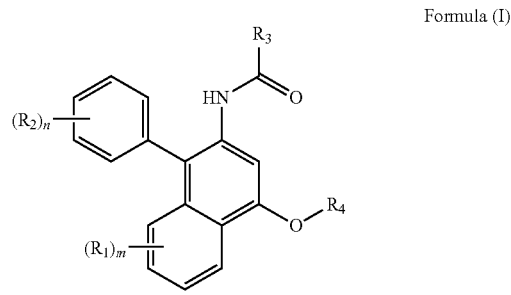

12 Claims, 1 Drawing Sheet

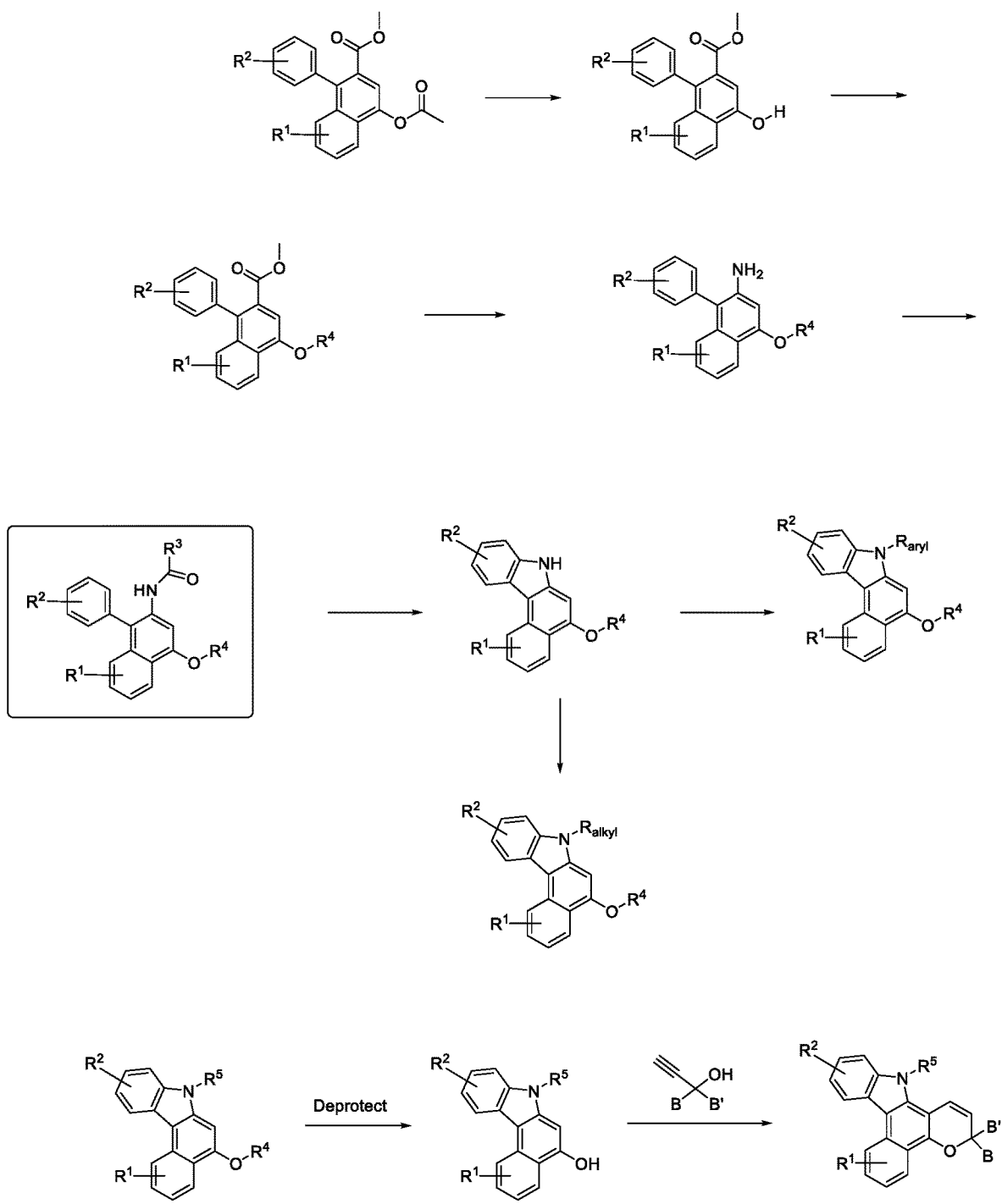

METHOD FOR PREPARING INDOLENAPHTHOPYRANS

CROSS-REFERENCE TO RELATED APPLICATION

The application is the United States national phase of International Application No. PCT/EP2018/086597 filed Dec. 21, 2018, the disclosure of which is hereby incorporated by reference in its entirety.

FIELD

The present invention relates to photochromic compounds, such as photochromic indolenaphthopyran compounds, and efficient methods for producing photochromic indolenaphthopyran compounds from phenylnaphthol synthetic intermediates.

BACKGROUND

Photochromic compounds undergo a transformation from one state (or form) to another state in response to certain wavelengths of electromagnetic radiation (e.g., "actinic radiation"). Each state has a characteristic absorption spectrum. For example, many photochromic compounds transform from an unactivated (e.g., bleached or substantially colorless) state to an activated (e.g., tinted) state upon exposure to actinic radiation. When the actinic radiation is removed, the photochromic compounds reversibly transform from the activated state back to the unactivated state.

The synthesis of photochromic indolenaphthopyran compounds has been described previously in WO 99/23071. A particular step in the preparation utilizes the azide synthetic intermediate depicted in Formula A below, which is photochemically decomposed in order to obtain the corresponding indolenaphthol compound depicted in Formula B. The indolenaphthol compound is further reacted to form an indolenaphthopyran compound.

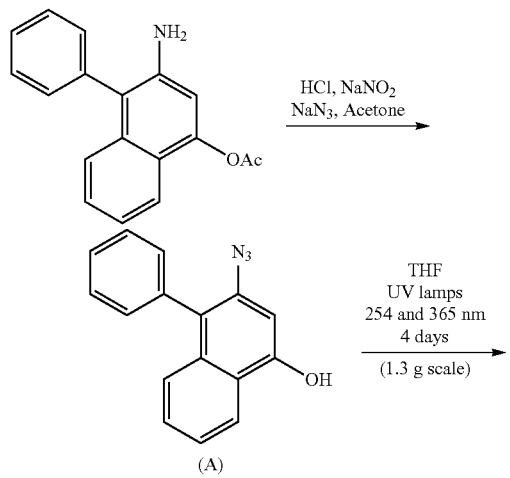

(A)

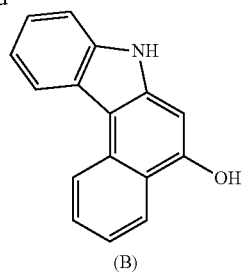

(B)

This synthetic route has several disadvantages. The UV light required for this photochemical reaction makes this step difficult to perform on a large scale, as the rate of the reaction is limited by the reactant's exposure to UV light. In addition, the production of the azide intermediate depicted in Formula A poses a safety hazard, due to the potential release of hydrazoic acid, an explosive liquid at room temperature and pressure, from the hydrolysis of sodium azide. Additionally, organic azide compounds must be handled carefully as they can be heat- and shock-sensitive and can explosively decompose. Therefore, it would be desirable to provide a process for producing photochromic indolenaphthopyran compounds which is scalable and avoids the preparation of azide intermediates.

The phenylnaphthol compounds of the present invention provide a useful synthetic intermediate for the preparation of photochromic indolenaphthopyran compounds. The process disclosed herein avoids the problems associated with the prior art methods, and provides a synthetic route for the preparation of photochromic compounds with scalable reactions that are amenable to a variety of substituents with good yields.

SUMMARY

Provided is a phenylnaphthol compound comprises a core skeletal structure represented by the following Formula (I),

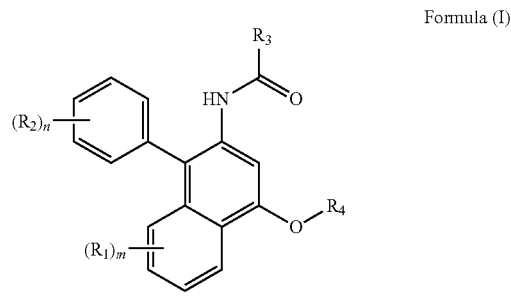

Formula (I)

wherein, m is 0 to 4, n is 0 to 4, $R^1$ and $R^2$ are each independently hydroxyl, cyano, (meth)acrylate, amino, halo, substituted or unsubstituted alkyl, boronic ester, boronic acid, polyether, polyester, polycarbonate, polyurethane, substituted or unsubstituted aryl, substituted or unsubstituted heterocycloaryl, substituted or unsubstituted heteroaryl, substituted or unsubstituted alkoxy, substituted or unsubstituted aryloxy, substituted or unsubstituted alkylthio, substituted or unsubstituted arylthio, ketone, aldehyde, ester, carboxylic acid, carboxylate, amide, carbonate, carbamate, urea, siloxane, alkoxysilane, or polysiloxane, and two $R^1$ groups and/or two $R^2$ groups on adjacent carbon atoms may connect to form a ring; $R^3$ is selected from substituted or unsubstituted 2-pyridyl or substituted or unsubstituted 2-quinolyl; and $R^4$ is selected from hydrogen, substituted or unsubstituted alkyl, alkoxymethyl, substituted or unsubstituted silyl, or acyl.

Also provided is a process for producing an indolenaphthol compound comprising the core skeletal structure represented by the following Formula (II):

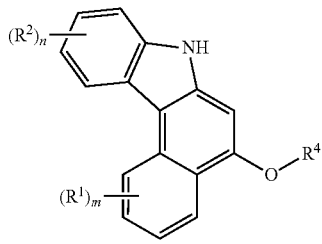

Formula (II)

wherein $R^1$, $R^2$, and $R^4$ are as described above, comprises cyclizing the phenylnaphthol compound depicted in Formula (I) in the presence of a catalyst.

The features that characterize the present invention are pointed out with particularity in the claims, which are annexed to and form a part of this disclosure. These and other features of the invention, its operating advantages and the specific objects obtained by its use will be more fully understood from the following detailed description in which non-limiting embodiments of the invention are illustrated and described.

BRIEF DESCRIPTION OF THE DRAWING

FIG. 1 illustrates a general scheme, Scheme 1, of an exemplary process of the invention for preparing photochromic indolenaphthopyran compounds.

DETAILED DESCRIPTION

As used herein, the articles "a", "an", and "the" include plural referents unless otherwise expressly and unequivocally limited to one referent.

As used herein, the term "includes" is synonymous with "comprises."

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

As used herein, unless otherwise indicated, left-to-right representations of linking groups, such as divalent linking groups, are inclusive of other appropriate orientations, such as, but not limited to, right-to-left orientations. For purposes of non-limiting illustration, the left-to-right representation of the divalent linking group

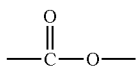

or equivalently —C(O)O—, is inclusive of the right-to-left representation thereof,

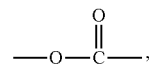

or equivalently —O(O)C— or —OC(O)—.

Other than in the operating examples, or where otherwise indicated, all numbers expressing quantities of ingredients, reaction conditions, and so forth used in the specification and claims are to be understood as modified in all instances by the term "about". By "about" is meant plus or minus twenty-five percent of the stated value, such as plus or minus ten percent of the stated value. However, this should not be considered as limiting to any analysis of the values under the doctrine of equivalents.

As used herein, molecular weight values of polymers, such as weight average molecular weights (Mw) and number average molecular weights (Mn), are determined by gel permeation chromatography using appropriate standards, such as polystyrene standards.

As used herein, the term "polymer" means homopolymers (e.g., prepared from a single monomer species), copolymers (e.g., prepared from at least two monomer species), and graft polymers.

As used herein, the term "(meth)acrylate" and similar terms, such as "(meth)acrylic acid ester" means derivatives of acrylic acid and methacrylic acid, inclusive of acrylate esters, methacrylate esters, acrylamides, methacrylamides, acrylic acid and methacrylic acid. As used herein, the term "(meth)acrylic acid" means methacrylic acid and/or acrylic acid.

The photochromic compounds of the present invention are, with some embodiments, also referred to herein as photochromic-dichroic compounds (such as, when they include one or more mesogen-containing groups).

The compounds of the present invention, as described herein, including, but not limited to, photochromic compounds represented by Formula (I), Formula (II), Formula (III), and Formula (IV), in each case can optionally further include one or more coproducts, resulting from the synthesis of such compounds.

As used herein, the term "photochromic" and similar terms, such as "photochromic compound", means having an absorption spectrum for at least visible radiation that varies in response to absorption of at least actinic radiation. Further, as used herein the term "photochromic material" means any substance that is adapted to display photochromic properties (such as, adapted to have an absorption spectrum for at least visible radiation that varies in response to absorption of at least actinic radiation) and which includes at least one photochromic compound.

As used herein, the term "actinic radiation" means electromagnetic radiation that is capable of causing a response in a material, such as, but not limited to, transforming a photochromic material from one form or state to another as will be discussed in further detail herein.

As used herein, the term "dichroic" means capable of absorbing one of two orthogonal plane polarized components of at least transmitted radiation more strongly than the other.

As used herein, the term "photochromic-dichroic" and similar terms, such as "photochromic-dichroic compound", means possessing and/or providing both photochromic properties (i.e., having an absorption spectrum for at least visible radiation that varies in response to at least actinic radiation), and dichroic properties (i.e., capable of absorbing one of two orthogonal plane polarized components of at least transmitted radiation more strongly than the other).

As used herein, and unless stated otherwise or otherwise limited, the term "photochromic material" includes thermally reversible photochromic materials and compounds and non-thermally reversible photochromic materials and compounds. The term "thermally reversible photochromic compounds/materials" as used herein means compounds/materials capable of converting from a first state, for example a "clear state," to a second state, for example a "colored state," in response to actinic radiation, and reverting back to the first state in response to thermal energy. The term "non-thermally reversible photochromic compounds/materials" as used herein means compounds/materials capable of converting from a first state, for example a "clear state," to a second state, for example a "colored state," in response to actinic radiation, and reverting back to the first state in response to actinic radiation of substantially the same wavelength(s) as the absorption(s) of the colored state (e.g., discontinuing exposure to such actinic radiation).

As used herein, to modify the term "state," the terms "first" and "second" are not intended to refer to any particular order or chronology, but instead refer to two different conditions or properties. For purposes of non-limiting illustration, the first state and the second state of a photochromic compound can differ with respect to at least one optical property, such as but not limited to the absorption of visible and/or UV radiation. Thus, according to various non-limiting embodiments disclosed herein, the photochromic compounds of the present invention can have a different absorption spectrum in each of the first and second state. For example, while not limiting herein, a photochromic compound of the present invention can be clear in the first state and colored in the second state. Alternatively, a photochromic compound of the present invention can have a first color in the first state and a second color in the second state.

As used herein, the term "optical" means pertaining to or associated with light and/or vision. For example, according to various non-limiting embodiments disclosed herein, the optical article or element or device can be chosen from ophthalmic articles, elements and devices; display articles, elements and devices; windows; mirrors; or active and passive liquid crystal cell articles, elements and devices.

As used herein, the term "ophthalmic" means pertaining to or associated with the eye and vision. Non-limiting examples of ophthalmic articles or elements include corrective and non-corrective lenses, including single vision or multi-vision lenses, which can be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intra-ocular lenses, magnifying lenses, and protective lenses or visors.

As used herein, the term "display" means the visible or machine-readable representation of information in words, numbers, symbols, designs or drawings. Non-limiting examples of display elements include screens, monitors, and security elements, such as security marks.

As used herein, the term "window" means an aperture adapted to permit the transmission of radiation therethrough. Non-limiting examples of windows include automotive and aircraft transparencies, windshields, filters, shutters, and optical switches.

As used herein, the term "mirror" means a surface that specularly reflects a large fraction of incident light.

As used herein, the term "liquid crystal cell" refers to a structure containing a liquid crystal material that is capable of being ordered. A non-limiting example of a liquid crystal cell element is a liquid crystal display.

As used herein, the terms "formed over", "deposited over", "provided over", "applied over", "residing over", or "positioned over" mean formed, deposited, provided, applied, residing, or positioned on but not necessarily in direct (or abutting) contact with the underlying element, or surface of the underlying element. For example, a layer "positioned over" a substrate does not preclude the presence of one or more other layers, coatings, or films of the same or different composition located between the positioned or formed layer and the substrate.

As used herein, recitations relating to ring positions such as, but not limited to, position-x (e.g., position-3 or position-13) means a particular position in the ring structure, such as the core skeletal structure, of a chemical compound, such as the indolenaphthopyran photochromic compounds of the present invention, and which are depicted herein in accordance with some embodiments by numbers within the ring structures of representative chemical formulas such as, but not limited to Formulas (I) and/or (Ia).

By "core skeletal structure" is meant a compound comprising at least the skeletal structure depicted in the associated Formula. The core skeletal structure is provided for purposes of identifying numbered ring positions. However, it is to be understood that, unless specifically shown to the contrary, the core skeletal structure(s) can have one or more atoms or one or more groups (not specifically illustrated on the corresponding Formula) bonded to one or more of the numbered ring positions on the core skeletal structure, which can be the same or different from one another.

The photochromic compounds of the present invention are referred to herein with reference to the term "core skeletal structure," which can be represented by one or more formulas, such as but not limited to Formulas (I), (II), (III), and/or (IV).

All documents or portions of documents, such as but not limited to issued patents and patent applications, referred to herein, and unless otherwise indicated, are to be considered to be "incorporated by reference" in their entirety.

"Aryl group" refers to an aromatic cyclic monovalent hydrocarbon radical, and the term "aromatic" refers to a cyclically conjugated hydrocarbon with a stability (due to delocalization) that is significantly greater than that of a hypothetical localized structure. Examples of aryl groups include $C_6$-$C_{14}$ aryl groups, such as, but not limited to, phenyl, naphthyl, phenanthryl, and anthracenyl.

As used herein, recitations of "halo substituted" and related terms (such as, but not limited to, haloalkyl groups, haloalkenyl groups, haloalkynyl groups, haloaryl groups and halo-heteroaryl groups) means a group in which at least one, and up to and including all of the available hydrogen groups thereof is substituted with a halo group. The term "halo-substituted" is inclusive of "perhalo-substituted." As used herein, the term perhalo-substituted group and related terms (such as, but not limited to, perhaloalkyl groups, perhaloalkenyl groups, perhaloalkynyl groups, perhaloaryl groups or perhalo-heteroaryl groups) means a group in which all of the available hydrogen groups thereof are substituted with a halo group. For example, perhalomethyl is —$CX_3$; perhalophenyl is —$C_6X_5$, where X represents one or more halo groups, such as, but not limited to F, Cl or Br.

As used herein, recitations of "linear or branched" groups, such as linear or branched alkyl, are herein understood to include: groups that are linear (or "straight chain"), such as linear $C_1$-$C_{25}$ alkyl groups; and groups that are appropriately branched, such as branched $C_3$-$C_{25}$ alkyl groups.

The term "alkyl" as used herein means linear or branched, cyclic or acyclic $C_1$-$C_{25}$ alkyl. Linear or branched alkyl can include $C_1$-$C_{25}$ alkyl, such as $C_1$-$C_{20}$ alkyl, such as $C_2$-$C_{10}$ alkyl, such as $C_1$-$C_{12}$ alkyl, such as $C_1$-$C_6$ alkyl. Examples of alkyl groups from which the various alkyl groups of the present invention can be selected from, include, but are not limited to, those recited further herein. Alkyl groups can include "cycloalkyl" groups. The term "cycloalkyl" as used herein means groups that are appropriately cyclic, such as, but not limited to, $C_3$-$C_{12}$ cycloalkyl (including, but not limited to, cyclic $C_5$-$C_7$ alkyl, or cyclic $C_3$-$C_{10}$ alkyl) groups. Examples of cycloalkyl groups include, but are not limited to, those recited further herein. The term "cycloalkyl" as used herein also includes: bridged ring polycycloalkyl groups (or bridged ring polycyclic alkyl groups), such as, but not limited to, bicyclo[2.2.1]heptyl (or norbornyl) and bicyclo[2.2.2]octyl; and fused ring polycycloalkyl groups (or fused ring polycyclic alkyl groups), such as, but not limited to, octahydro-1H-indenyl, and decahydronaphthalenyl.

The term "heterocycloalkyl" as used herein means groups that are appropriately cyclic, such as, but not limited to, $C_2$-$C_{12}$ heterocycloalkyl groups, such as $C_5$-$C_7$ heterocycloalkyl groups, such as $C_2$-$C_{10}$ heterocycloalkyl groups, and which have at least one hetero atom in the cyclic ring, such as, but not limited to, O, S, N, P, and combinations thereof. Examples of heterocycloalkyl groups include, but are not limited to, imidazolyl, tetrahydrofuranyl, tetrahydropyranyl and piperidinyl. The term "heterocycloalkyl" as used herein also includes: bridged ring polycyclic heterocycloalkyl groups, such as, but not limited to, 7-oxabicyclo[2.2.1]heptanyl; and fused ring polycyclic heterocycloalkyl groups, such as, but not limited to, octahydrocyclopenta[b]pyranyl, and octahydro-1H-isochromenyl.

The term "heteroaryl", as used herein, includes, but is not limited to, $C_3$-$C_{18}$ heteroaryl, such as, but not limited to, $C_3$-$C_{10}$ heteroaryl (including fused ring polycyclic heteroaryl groups) and means an aryl group having at least one hetero atom in the aromatic ring, or in at least one aromatic ring in the case of a fused ring polycyclic heteroaryl group. Examples of heteroaryl groups include, but are not limited to, furanyl, pyranyl, pyridinyl, isoquinoline, and pyrimidinyl.

As used herein, the term "fused ring polycyclic-aryl-alkyl group" and similar terms such as fused ring polycyclic-alkyl-aryl group, fused ring polycyclo-aryl-alkyl group, and fused ring polycyclo-alkyl-aryl group means a fused ring polycyclic group that includes at least one aryl ring and at least one cycloalkyl ring that are fused together to form a fused ring structure. For purposes of non-limiting illustration, examples of fused ring polycyclic-aryl-alkyl groups include, but are not limited to indenyl, 9H-flourenyl, cyclopentanaphthenyl, and indacenyl.

The term "aralkyl", as used herein, includes, but is not limited to, $C_6$-$C_{24}$ aralkyl, such as, but not limited to, $C_6$-$C_{10}$ aralkyl, and means an alkyl group substituted with an aryl group. Examples of aralkyl groups include, but are not limited to, benzyl and phenethyl.

Representative alkyl groups include, but are not limited to, methyl, ethyl, propyl, isopropyl, butyl, isobutyl, sec-butyl, tert-butyl, pentyl, neopentyl, hexyl, heptyl, octyl, nonyl and decyl. Representative alkenyl groups include, but are not limited to, vinyl, allyl and propenyl. Representative alkynyl groups include, but are not limited to, ethynyl, 1-propynyl, 2-propynyl, 1-butynyl, and 2-butynyl. Representative cycloalkyl groups include, but are not limited to, cyclopropyl, cyclobutyl, cyclopentyl, cyclohexyl, and cyclooctyl substituents. Representative heterocycloalkyl groups include, but are not limited to, imidazolyl, tetrahydrofuranyl, tetrahydropyranyl and piperidinyl. Representative aryl groups include, but are not limited to, phenyl, naphthyl, anthracynyl, phenanthrenyl, and tetracenyl (including structural isomers thereof). Representative heteroaryl groups include, but are not limited to, furanyl, pyranyl, pyridinyl, isoquinolinyl, and pyrimidinyl. Representative aralkyl groups include, but are not limited to, benzyl and phenethyl.

The term "nitrogen-containing heterocycle", as used herein, includes, but is not limited to, a nitrogen-containing ring wherein the nitrogen-containing ring is bonded through a ring nitrogen. Examples of nitrogen-containing heterocycles include, but are not limited to, cyclic aminos, such as morpholino, piperidino, and pyrrolidino; and heteroaromatics, such as imidazole, pyrrole, indole, and carbazole.

The term "acyl", as used herein, includes, but is not limited to, alkanoyl or aryloyl groups with the formula $R_aCO$—, wherein $R_a$ represents a substituted or unsubstituted alkyl group or a substituted or unsubstituted aryl group.

As used herein, the term "polysiloxane", such as with regard to substituents of various groups of the photochromic compounds of the present invention, includes a material represented by the following Formula (G):

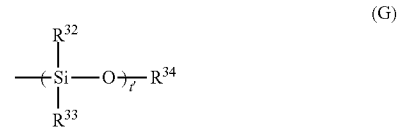

(G)

With reference to Formula (G), subscript t' is from 2 to 200, such as from 2 to 100, or 2 to 50, or from 2 to 25, or from 2 to 15, or from 2 to 10, or from 2 to 5, in each case inclusive of the recited values. With further reference to Formula (G): $R^{32}$ and $R^{33}$, for each t', are each independently selected from alkyl or aryl; and $R^{34}$ is selected from hydrogen, alkyl, or aryl. With some embodiments: $R^{32}$ and $R^{33}$ for each t', are each independently selected from methyl, ethyl, or phenyl; and $R^{34}$ is selected from hydrogen, methyl, ethyl, or phenyl.

As used herein, the term "polysiloxane", such as with regard to substituents of various groups of the photochromic compounds of the present invention, alternatively to or in addition to a material represented by Formula (G), includes a material represented by the following Formula (H):

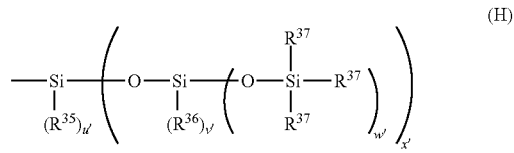

(H)

With reference to Formula (H), subscript u' is 0-2 and subscript x' is 1-3, provided that u'+x' is 3; and subscript v' is 0-2 and subscript w' is 1-3, provided that v'+w' is 3. With further reference to Formula (H), $R^{31}$ independently for each u', $R^{36}$ independently for each v' and each x', and each $R^{37}$ independently for each w' and each x', are in each case independently selected from alkyl (such as, but not limited to, methyl or ethyl) or aryl (such as, but not limited to, phenyl).

As used herein, recitations of "substituted" group means a group including, but not limited to, alkyl group, heterocycloalkyl group, aryl group, and/or heteroaryl group, in which at least one hydrogen thereof has been replaced or substituted with a group that is other than hydrogen, such as, but not limited to, alkoxy groups; halo groups (e.g., F, Cl, I, and Br); hydroxyl groups; thiol groups; alkylthio groups; arylthio groups; ketone groups; aldehyde groups; ester groups; carboxylic acid groups; phosphoric acid groups; phosphoric acid ester groups; sulfonic acid groups; sulfonic acid ester groups; nitro groups; cyano groups; alkyl groups (including aralkyl groups); alkenyl groups; alkynyl groups; haloalkyl groups; perhaloalkyl groups; heterocycloalkyl groups; aryl groups (including alkaryl groups, including hydroxyl substituted aryl, such as phenol, and including poly-fused-ring aryl); heteroaryl groups (including poly-fused-ring heteroaryl groups); amino groups, such as —N($R^{11'}$)($R^{12'}$) where $R^{11'}$ and $R^{12'}$ are each independently selected, for example, from hydrogen, alkyl, heterocycloalkyl, aryl, or heteroaryl; carboxylate groups; siloxane groups; alkoxysilane groups; polysiloxane groups; amide groups; carbamate groups; carbonate groups; urea groups; polyester groups; polyether groups; polycarbonate groups; polyurethane groups; acrylate groups; methacrylate groups; nitrogen-containing heterocycles; or combinations thereof, including those classes and examples as described further herein.

As used herein, the terms "phenylnaphthol" and "indolenaphthol" include protected phenylnaphthol and indolenaphthol compounds, and phenylnaphthol and indolenaphthol derivatives.

As used herein, "at least one of" is synonymous with "one or more of", whether the elements are listed conjunctively or disjunctively. For example, the phrases "at least one of A, B, and C" and "at least one of A, B, or C" each mean any one of A, B, or C, or any combination of any two or more of A, B, or C. For example, A alone; or B alone; or C alone; or A and B; or A and C; or B and C; or all of A, B, and C.

As used herein, "selected from" is synonymous with "chosen from" whether the elements are listed conjunctively or disjunctively. For example, the phrases "selected from A, B, and C" and "selected from A, B, or C" each mean any one of A, B, or C, or any combination of any two or more of A, B, or C. For example, A alone; or B alone; or C alone; or A and B; or A and C; or B and C; or all of A, B, and C.

The discussion of the invention may describe certain features as being "particularly" or "preferably" within certain limitations (e.g., "preferably", "more preferably", or "even more preferably", within certain limitations). It is to be understood that the invention is not limited to these particular or preferred limitations but encompasses the entire scope of the disclosure.

The invention comprises, consists of, or consists essentially of, the following aspects of the invention, in any combination.

The compounds according to the present invention can be represented by one or more of the core skeletal structures described below.

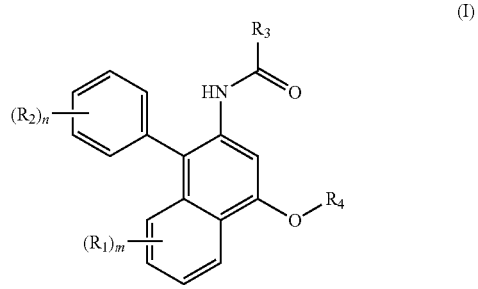

(I)

With reference to Formula (I), $R^1$ and $R^2$ are each independently hydroxyl, cyano, (meth)acrylate, amino, halo such as fluoro, chloro, bromo, or iodo, substituted or unsubstituted alkyl, boronic ester or boronic acid, polyether, polyester, polycarbonate, polyurethane, substituted or unsubstituted aryl, substituted or unsubstituted heterocycloalkyl, substituted or unsubstituted heteroaryl, substituted or unsubstituted alkoxy, substituted or unsubstituted aryloxy, substituted or unsubstituted alkylthio, substituted or unsubstituted arylthio, ketone, aldehyde, ester, carboxylic acid, carboxylate, amide, carbonate, carbamate, urea, siloxane, alkoxysilane, or polysiloxane. Two $R^1$ groups or two $R^2$ groups on adjacent carbon atoms may connect to form a ring. $R^3$ is selected from substituted or unsubstituted 2-pyridyl or substituted or unsubstituted 2-quinolyl. The substituents of the substituted 2-pyridyl and substituted 2-quinolyl groups are each independently selected from substituted or unsubstituted alkyl, substituted or unsubstituted alkoxy, substituted or unsubstituted aryloxy, substituted or unsubstituted aryl, substituted or unsubstituted heteroaryl, halogen, amino, ester, carboxylate, or hydroxyl. $R^4$ is selected from hydrogen, substituted or unsubstituted alkyl, alkoxymethyl, substituted or unsubstituted silyl, or acyl.

Examples of groups from which $R^1$ can be selected include, but are not limited to, halo, such as fluoro, substituted or unsubstituted alkyl, such as methyl, substituted or unsubstituted heteroaryl, substituted or unsubstituted alkoxy, such as methoxy, substituted or unsubstituted alkylthio, or substituted or unsubstituted arylthio. Examples of groups from which $R^2$ can be selected include, but are not limited to, halo, such as fluoro, substituted or unsubstituted alkyl, such as methyl or trifluoromethyl, substituted or unsubstituted heteroaryl, substituted or unsubstituted alkoxy, substituted or unsubstituted alkylthio, or substituted or unsubstituted arylthio. Examples of groups from which $R^3$ can be selected include, but are not limited to, 2-pyridyl. Examples of groups from which $R^4$ can be selected include, but are not limited to, substituted or unsubstituted alkyl, such as benzyl or substituted benzyl, substituted silyl, such as trialkylsilyl, such as trimethylsilyl, alkoxymethyl, such as methoxymethyl, or acyl, such as acetyl or benzoyl.

The compounds of the present invention can be prepared in accordance with art-recognized methods as follows. For purposes of non-limiting illustration and with reference to FIG. 1, general synthetic Scheme 1, the preparation of compounds according to the present invention is described as follows. Further detailed descriptions of the preparation of compounds of the present invention are provided further herein in the Examples. In FIG. 1, the various groups, such as $R^1$, $R^2$, $R^3$, $R^4$, B, B', $R_{aryl}$, and $R_{alkyl}$ of the various intermediates, reactants, and/or compounds depicted, are each as described herein, and/or represent precursors of such groups.

The synthesis of compounds depicted below as Formula (Ia) has been described in numerous references such as U.S. Pat. No. 6,296,785 or 7,262,295, with varying substituents.

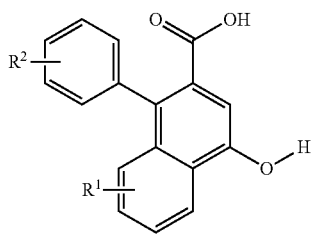

The hydroxyl group and the carboxylic acid group can be protected. For example, the hydroxyl group can be benzylated by reacting with benzyl chloride and a base such as sodium or potassium carbonate, to form a compound where $R^4$ is benzyl. The carboxylic ester that is formed can then be converted to the carboxylic acid by either acid or basic methods for ester hydrolysis. The resulting product is depicted below as Formula (Ib).

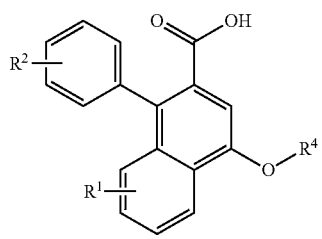

The carboxylic acid group can then be converted to an $NH_2$ group via Curtius rearrangement conditions using diphenyl phosphorylazide which generates the isocyanate group followed by hydrolysis to yield the amine group, as depicted below in Formula (Ic).

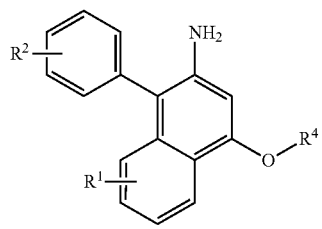

The amine group is converted to an amide group, as depicted in Formula (I), by traditional amide forming reactions such as reacting the amine with acid chlorides, esters, or carboxylic acid groups. For example, reaction of the amine with picolinoyl chloride with a base such as triethylamine gives the picolinamide, where $R_3$ is 2-pyridyl, in high yields.

The process according to the present invention is directed to producing an indolenaphthol compound comprising the core skeletal structure represented below in Formula (II).

Formula (II)

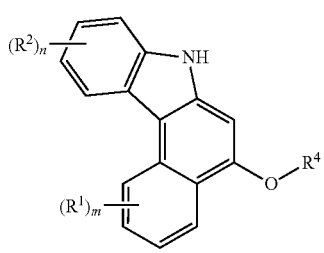

With respect to Formula (II), m, n, $R^1$, $R^2$, and $R^4$ are as described above as in Formula (I).

The process for producing an indolenaphthol compound comprises cyclizing the phenylnaphthol compound depicted in Formula (I) in the presence of a catalyst. See reaction depicted below. The catalyst may be a transition metal catalyst. Suitable transition metal catalysts may comprise copper, zinc, palladium, platinum, rhodium, or iridium. The cyclization may be performed with a copper catalyst as described in Takumatso, K. et al. *Org. Lett.* 2014, 16, 2892.

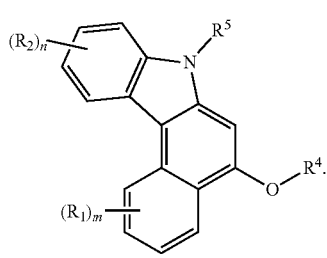

The process of the invention may further comprise alkylating or arylating the indolenaphthol compound of Formula (II) to produce an indolenaphthol compound comprising the core skeletal structure represented below in Formula (III).

Formula (III)

With respect to Formula (III), m, n, $R^1$, $R^2$, and $R^4$ are as described above as in Formula (I). $R^5$ is selected from substituted or unsubstituted alkyl, substituted or unsubstituted aryl, or acyl. Examples of groups from which $R^5$ can be selected include, but are not limited to, alkyl, phenyl, or substituted phenyl. Non-limiting suitable alkylation and arylation reactions of the process are described below.

The alkylation of the indole group as depicted in Formula (IIIa) can be accomplished by reaction with an alkyl halide, triflate, or tosylate in the presence of a base. Suitable bases include sodium or potassium tertbutoxide. The indole can be deprotonated by strong base such as sodium hydride or n-butyl lithium and then the anion reacted with the alkyl halide, triflate, or tosylate. See reaction depicted below.

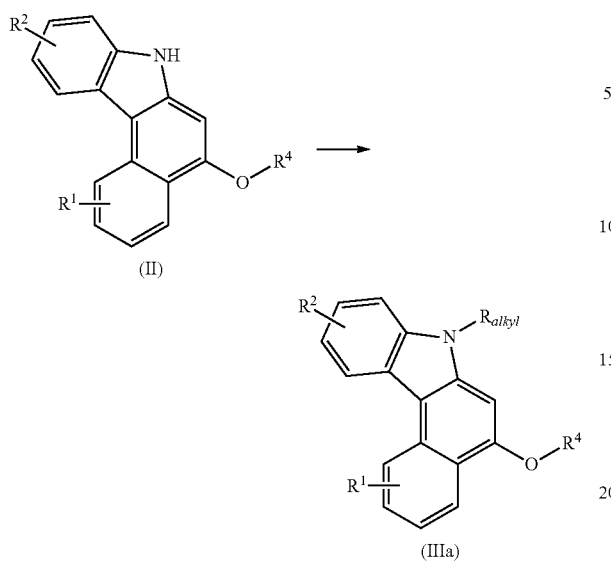

(II)

(IIIa)

The indole group can be arylated, as depicted in Formula (IIIb), by a cross coupling reaction with a transition metal catalyst and an aryl halide. The cross coupling reaction may be an Ullmann coupling reaction with a copper catalyst and an aryl halide, such as phenyl halide. See reaction depicted below.

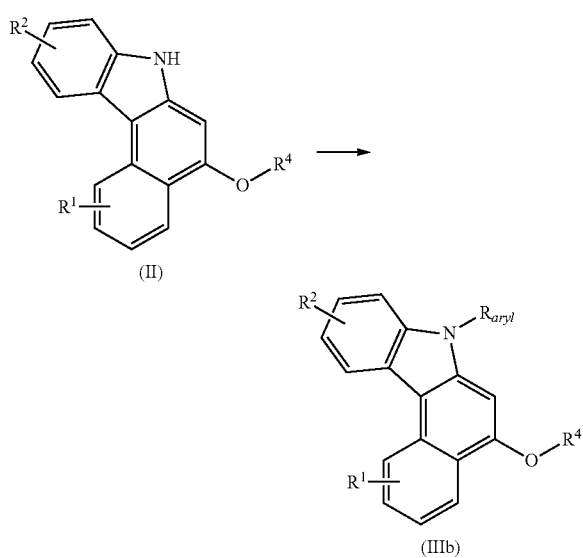

(II)

(IIIb)

The indole can also be arylated as depicted in Formula (IIIb) via nucleophilic aromatic substitution, such as by reaction with an aryl fluoride in a suitable solvent such as tetrahydrofuran or dimethylformamide.

The process of the invention may further comprise deprotecting $R^4$ to generate a hydroxyl group, when $R^4$ is substituted or unsubstituted alkyl, alkoxymethyl, substituted or unsubstituted silyl, or acyl. The protecting group can be removed by palladium hydrogenation conditions or with a strong acid. See reaction depicted below, wherein $R^4$ of Formula (III) is substituted or unsubstituted alkyl, alkoxymethyl, substituted or unsubstituted silyl, or acyl, and the deprotected product is shown in Formula (IIId).

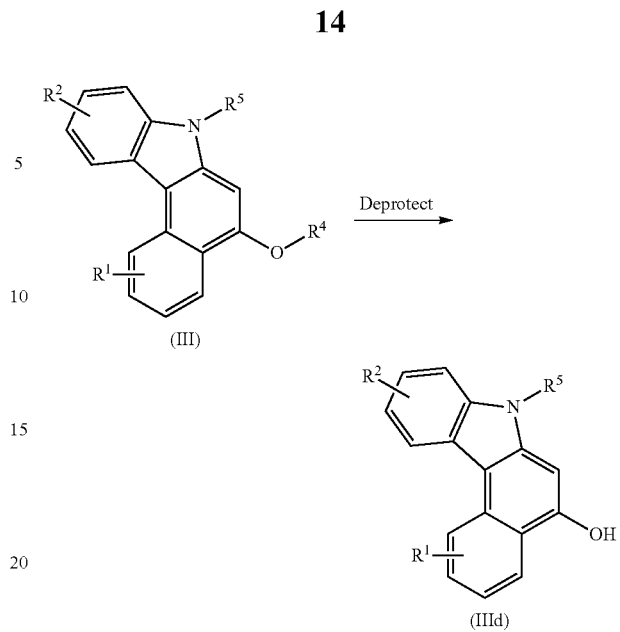

(III)

(IIId)

The process may further comprise reacting with a diaryl propargyl alcohol to form an indolenaphthopyran compound comprising the core skeletal structure depicted below in Formula (IV).

Formula (IV)

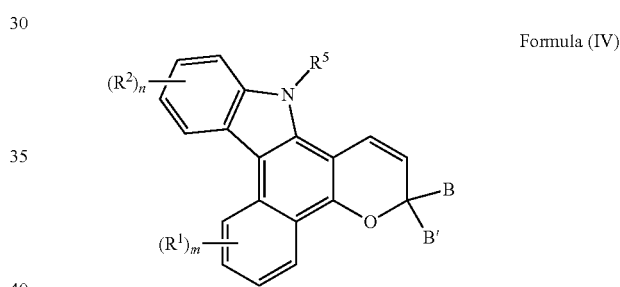

With respect to Formula (IV), m, n, $R^1$, $R^2$, and $R^4$ are as described above as in Formula (I), and $R^5$ is as described above as in Formula (III). B and B' are each independently selected from substituted or unsubstituted aryl, or substituted or unsubstituted heteroaryl. B and B' can each independently be substituted or unsubstituted phenyl. Each phenyl substituent can be selected from alkoxy, halo, alkyl, or aryloxy.

The indolenaphthol compound depicted in Formula (III) can be reacted with aryl propargyl alcohols under acidic conditions to yield indolenaphthopyran compounds, as depicted in Formula (IV). See reaction depicted below.

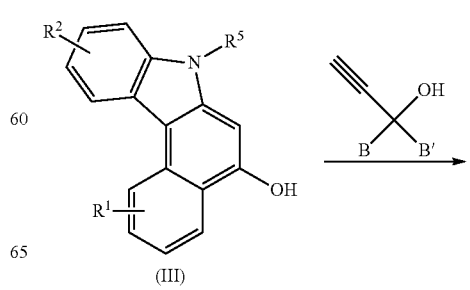

(III)

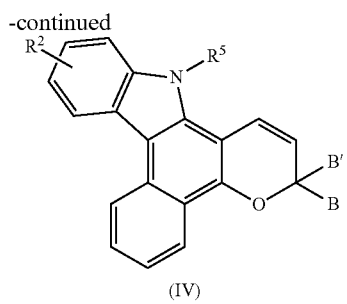

(IV)

The photochromic indolenaphthopyran compounds prepared in accordance with the process of the present invention, such as those described with reference to Formula (IV) above can each be used alone, or in combination with one or more other photochromic compounds. For example, the photochromic compounds of the present invention can be used in conjunction with one or more other photochromic compounds having activated absorption maxima within the range of 300 to 1,000 nanometers. Further, the indolenaphthopyran compounds prepared according to the present invention can be used in conjunction with one or more complementary conventional polymerizable or compatibilized photochromic compounds, such as for example, those disclosed in U.S. Pat. No. 6,113,814 (at col. 2, line 39 to col. 8, line 41), and U.S. Pat. No. 6,555,028 (at col. 2, line 65 to col. 12, line 56); or in combination with a mixture of other photochromic compounds to attain certain activated colors, such as a near neutral gray or near neutral brown. See, for example, U.S. Pat. No. 5,645,767, col. 12, line 66 to col. 13, line 19, which describes the parameters that define neutral gray and brown colors.

The indolenaphthopyran compounds prepared according to the present invention, can be used solely or in combination with other photochromic compounds as discussed immediately above to prepare photochromic compositions. For example, such photochromic compositions can include: (i) an organic material, in which the organic material is at least one of a polymeric material, an oligomeric material, or a monomeric material; and (ii) an indolenaphthopyran photochromic compound (either alone or in combination with other photochromic compounds) as prepared in accordance with the present invention, which is incorporated into at least a portion of the organic material. Examples of suitable organic materials can include but are not limited to any of those chosen from a polymeric material, an oligomeric material and/or a monomeric material, with some embodiments. Examples of polymeric materials that can be used with the photochromic compositions of the present invention include, but are not limited to: poly(carbonate), copolymers of ethylene and vinyl acetate; copolymers of ethylene and vinyl alcohol; copolymers of ethylene, vinyl acetate, and vinyl alcohol (such as those that result from the partial saponification of copolymers of ethylene and vinyl acetate); cellulose acetate butyrate; poly(urethane); poly(acrylate); poly(methacrylate); epoxies; aminoplast functional polymers; poly(anhydride); poly(urea urethane); N-alkoxymethyl(meth)acrylamide functional polymers; poly(siloxane); poly(silane); and combinations and mixtures thereof. Further classes and examples of polymeric materials that can be used with the photochromic compositions of the present invention include, but are not limited to, those disclosed at column 39, line 45 through column 40, line 67 of U.S. Pat. No. 9,028,728 B2. Such photochromic compositions can include additive materials such as a photoinitiator, a thermal initiator, a polymerization inhibitor, a solvent, a light stabilizer, a heat stabilizer, a mold release agent, a rheology control agent, a leveling agent, a free radical scavenger, and/or an adhesion promoter. The photochromic composition according to the present invention can be a photochromic coating composition which can be in the form of art-recognized liquid coatings and powder coatings. The photochromic coating compositions of the present invention can be thermoplastic or thermosetting or curable coating compositions. Such compositions can be used to prepare photochromic articles such as ophthalmic articles, display articles, windows, mirrors, active liquid crystal cell articles, and passive liquid crystal cell articles. Such photochromic articles, e.g., photochromic lenses, can transition from a first unactivated state (e.g., clear and non-blue blocking state) to a second activated state (e.g., colored and blue-blocking state) upon exposure to actinic radiation. The articles can revert back to the first unactivated (and clear) state upon removal of the actinic radiation source. Thus, the photochromic articles according to the present invention provide enhanced protection from health risks associated with blue light exposure during outdoor activity, while maintaining acceptable aesthetics indoors.

The present invention is more particularly described in the following examples, which are intended as illustrative only, since numerous modifications and variations therein will be apparent to those skilled in the art.

EXAMPLES

The following examples are provided to illustrate compounds of the invention, the process for producing compounds of the invention, and processes for using such compounds to prepare photochromic compounds. The Examples provides descriptions of the synthesis of phenylnaphthol compounds of the invention and descriptions of the process of the invention for producing indolenaphthol and indolenaphthopyran compounds.

Preparation of Examples 1-10

In the following examples, representative synthetic procedures for preparing benzyl-protected phenylnaphthol and indolenaphthol compounds are detailed.

Example 1

A scheme for the synthesis of Example 1 is depicted below. "Ac" refers to acetyl, "Bn" refers to benzyl, "DPPA" refers to diphenylphosphoryl azide, "EtOH" refers to ethanol, "DCC" refers to N,N'-dicyclohexylcarbodiimide, "DMF" refers to dimethylformamide, "iPrOH" refers to isopropanol, "DMAP" refers to 4-(dimethylamino)pyridine, and "DCM" refers to dichloromethane. Each step of the synthesis is further described below.

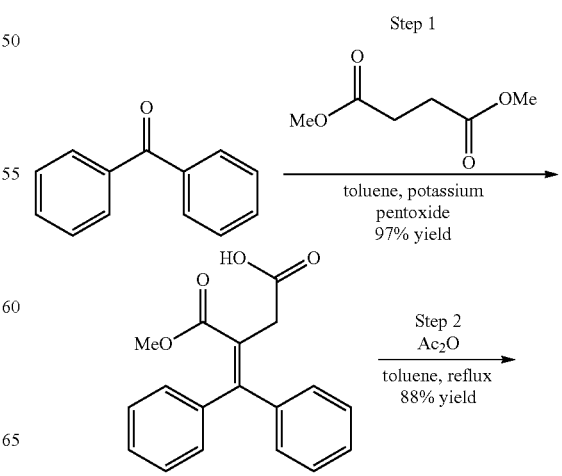

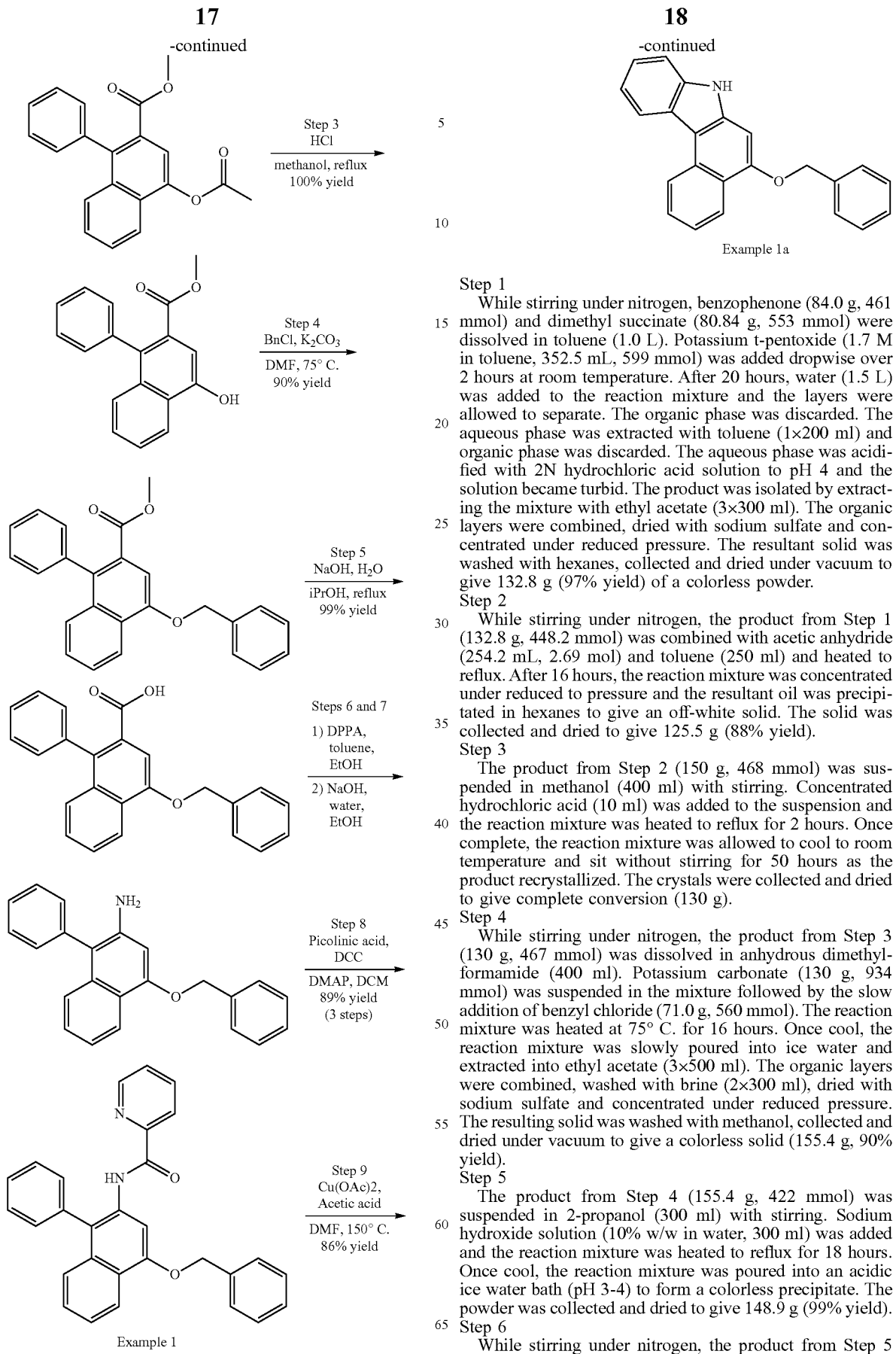

Example 1a

Step 1
While stirring under nitrogen, benzophenone (84.0 g, 461 mmol) and dimethyl succinate (80.84 g, 553 mmol) were dissolved in toluene (1.0 L). Potassium t-pentoxide (1.7 M in toluene, 352.5 mL, 599 mmol) was added dropwise over 2 hours at room temperature. After 20 hours, water (1.5 L) was added to the reaction mixture and the layers were allowed to separate. The organic phase was discarded. The aqueous phase was extracted with toluene (1×200 ml) and organic phase was discarded. The aqueous phase was acidified with 2N hydrochloric acid solution to pH 4 and the solution became turbid. The product was isolated by extracting the mixture with ethyl acetate (3×300 ml). The organic layers were combined, dried with sodium sulfate and concentrated under reduced pressure. The resultant solid was washed with hexanes, collected and dried under vacuum to give 132.8 g (97% yield) of a colorless powder.

Step 2
While stirring under nitrogen, the product from Step 1 (132.8 g, 448.2 mmol) was combined with acetic anhydride (254.2 mL, 2.69 mol) and toluene (250 ml) and heated to reflux. After 16 hours, the reaction mixture was concentrated under reduced to pressure and the resultant oil was precipitated in hexanes to give an off-white solid. The solid was collected and dried to give 125.5 g (88% yield).

Step 3
The product from Step 2 (150 g, 468 mmol) was suspended in methanol (400 ml) with stirring. Concentrated hydrochloric acid (10 ml) was added to the suspension and the reaction mixture was heated to reflux for 2 hours. Once complete, the reaction mixture was allowed to cool to room temperature and sit without stirring for 50 hours as the product recrystallized. The crystals were collected and dried to give complete conversion (130 g).

Step 4
While stirring under nitrogen, the product from Step 3 (130 g, 467 mmol) was dissolved in anhydrous dimethylformamide (400 ml). Potassium carbonate (130 g, 934 mmol) was suspended in the mixture followed by the slow addition of benzyl chloride (71.0 g, 560 mmol). The reaction mixture was heated at 75° C. for 16 hours. Once cool, the reaction mixture was slowly poured into ice water and extracted into ethyl acetate (3×500 ml). The organic layers were combined, washed with brine (2×300 ml), dried with sodium sulfate and concentrated under reduced pressure. The resulting solid was washed with methanol, collected and dried under vacuum to give a colorless solid (155.4 g, 90% yield).

Step 5
The product from Step 4 (155.4 g, 422 mmol) was suspended in 2-propanol (300 ml) with stirring. Sodium hydroxide solution (10% w/w in water, 300 ml) was added and the reaction mixture was heated to reflux for 18 hours. Once cool, the reaction mixture was poured into an acidic ice water bath (pH 3-4) to form a colorless precipitate. The powder was collected and dried to give 148.9 g (99% yield).

Step 6
While stirring under nitrogen, the product from Step 5 (149.1 g, 421 mmol) was suspended in anhydrous toluene (800 ml). Triethylamine (111 g, 1.1 mol) and absolute ethanol (100 ml) were added dissolving the suspension. Diphenylphosphoryl azide (174 g, 632 mmol) was added portion-wise to the reaction mixture that exothermed to reflux on its own accord and heat was added to reflux for a total of 2 hours. Once cool, the reaction mixture was added to water (1.5 L) and ethyl acetate (500 ml) and the layers were separated. The organic layer was washed with water (3×1 L), dried with sodium sulfate and concentrated under reduced pressure to give a reddish oil that was used without further purification.

Step 7

The resultant oil from Step 6 was dispersed in tetrahydrofuran (600 ml), ethanol (400 ml) and water (1.1 L) with sodium hydroxide (86 g, 2.2 mol). The reaction mixture was heated to reflux for 5 days. Once cool, brine (200 ml) was added to the reaction mixture, the layers were separated and the aqueous layer was washed with ethyl acetate (3×300 ml). The organic layers were combined, dried with sodium sulfate and concentrated under reduced pressure to give a reddish semi-solid that was used without further purification.

Step 8, Example 1

While stirring under nitrogen, the product from Step 7 was taken up in dichloromethane (1.2 L). Picolinic acid (78 g, 632 mmol) and 4-(dimethlyamino)pyridine (5.2 g, 42 mmol) were added followed by N,N'-dicyclohexylcarbodiimide (130.4 g, 632 mmol). The reaction mixture was allowed to stir at room temperature for 16 hours. The reaction mixture was filtered and concentrated under reduced pressure to give a black solid that was washed with methanol to give the protected phenylnaphthol compound (Example 1) as an off-white powder (160.85 g, 89% yield for 3 steps).

Step 9, Example 1a

While stirring under nitrogen, the product from step 8 (76.5 g, 178 mmol) was dissolved in anhydrous dimethylformamide (500 ml) and to this was added copper (II) acetate (65.0 g, 356 mmol) and glacial acetic acid (10.7 g, 178 mmol). The reaction mixture was heated to 150° C. for 20 hours to give 70% conversion of the starting material. The reaction mixture was filtered over a celite pad and the pad was washed with 500 ml of ethyl acetate. The filtrate was added to separatory funnel with water (1.0 L) containing ethylenediamine (10 ml) and the layers were separated. The organic layer was washed with water (3×300 ml), dried with sodium sulfate and concentrated under reduced pressure to give an off-white solid. The material was subjected to a second iteration of the reaction conditions and same isolation procedures. The resulting solid was washed twice with methanol (300 ml) to give an off-white powder (Example 1a, 49.5 g 86% yield). The product was confirmed by $^1$H NMR and mass spectrometry.

Examples 2-9 and Examples 2a-9a were prepared in a similar manner and are summarized in Table 1. All compounds were characterized by $^1$H NMR and mass spectrometry.

TABLE 1

| Example | Protected Phenylnaphthol | Yield[1] (%) |
|---|---|---|
| 1 | | 89 |
| 2 | | 65 |

TABLE 1-continued
| | | |
|---|---|---|
| 3 | 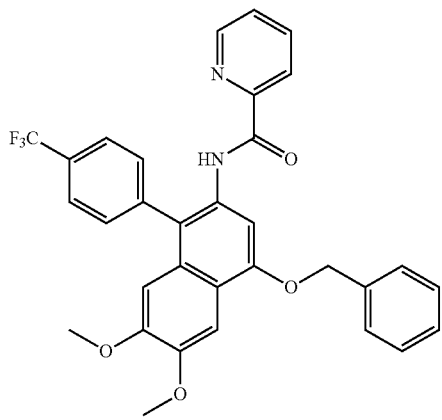 [SMILES: COc1cc2c(OCc3ccccc3)cc(NC(=O)c3ccccn3)c(-c3ccc(C(F)(F)F)cc3)c2cc1OC] | 96 |
| 4 | 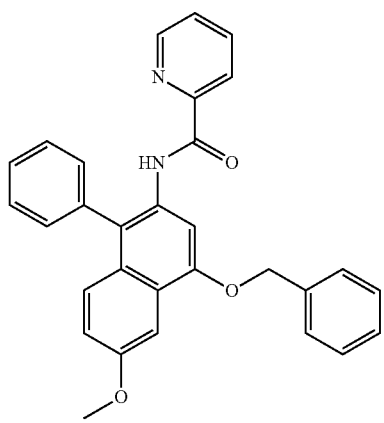 [SMILES: COc1ccc2c(-c3ccccc3)c(NC(=O)c3ccccn3)cc(OCc3ccccc3)c2c1] | 85 |
| 5 | 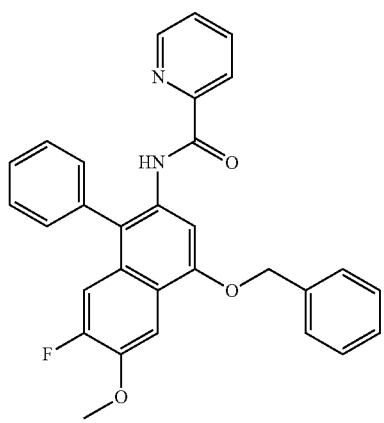 [SMILES: COc1cc2c(OCc3ccccc3)cc(NC(=O)c3ccccn3)c(-c3ccccc3)c2cc1F] | 86 |
| 6 | 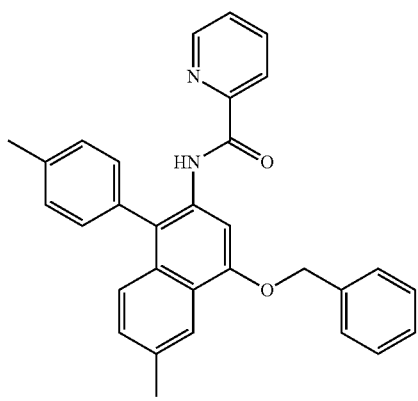 [SMILES: Cc1ccc(-c2c(NC(=O)c3ccccn3)cc(OCc3ccccc3)c3cc(C)ccc23)cc1] | 86 |

TABLE 1-continued
| | | |
|---|---|---|
| 7 | 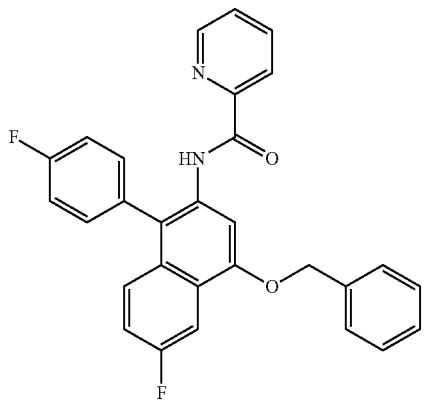 [SMILES: O=C(Nc1cc(OCc2ccccc2)c2cc(F)ccc2c1-c1ccc(F)cc1)c1ccccn1] | 30 |
| 8 | 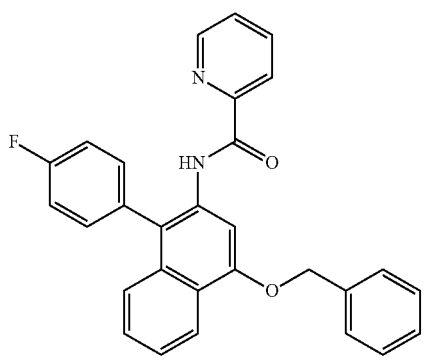 [SMILES: O=C(Nc1cc(OCc2ccccc2)c2ccccc2c1-c1ccc(F)cc1)c1ccccn1] | 79 |
| 9 | 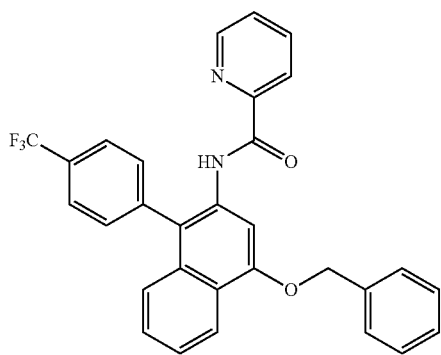 [SMILES: O=C(Nc1cc(OCc2ccccc2)c2ccccc2c1-c1ccc(C(F)(F)F)cc1)c1ccccn1] | 87 |
| 10 | 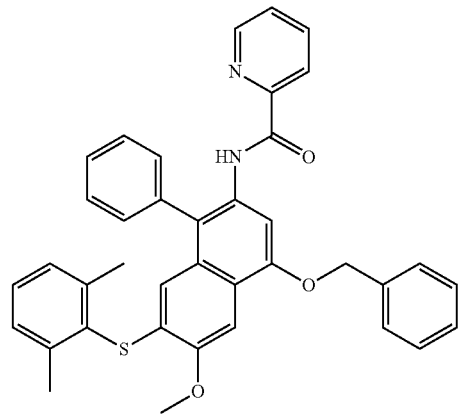 [SMILES: COc1cc2c(OCc3ccccc3)cc(NC(=O)c3ccccn3)c(-c3ccccc3)c2cc1Sc1c(C)cccc1C] | 70 |

TABLE 1-continued

| Example | Protected Indolenaphthol | Yield[2] (%) |
|---|---|---|
| 1a | | 86 |
| 2a | | 82 |
| 3a | | 91 |
| 4a | | 80 |
| 5a | | 71 |

TABLE 1-continued
| | | |
|---|---|---|
| 6a | 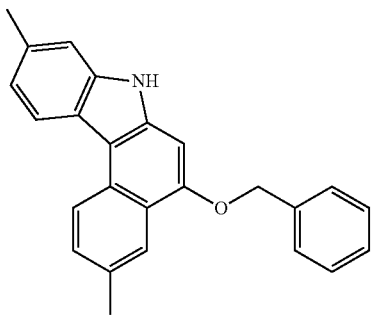 [SMILES: Cc1ccc2c(c1)[nH]c1cc(OCc3ccccc3)c3cc(C)ccc3c12] | 79 |
| 7a | 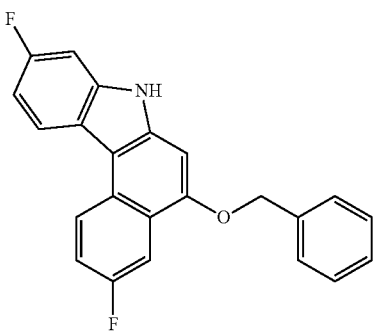 [SMILES: Fc1ccc2c(c1)[nH]c1cc(OCc3ccccc3)c3cc(F)ccc3c12] | 76 |
| 8a | 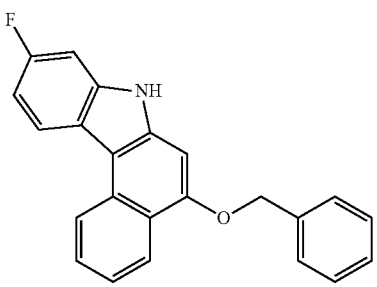 [SMILES: Fc1ccc2c(c1)[nH]c1cc(OCc3ccccc3)c3ccccc3c12] | 88 |
| 9a | 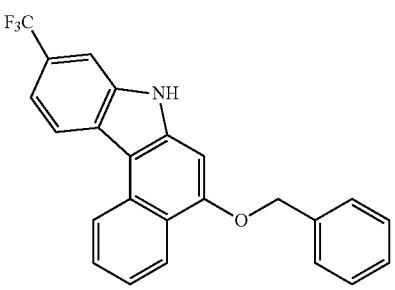 [SMILES: FC(F)(F)c1ccc2c(c1)[nH]c1cc(OCc3ccccc3)c3ccccc3c12] | 87 |
| 10a | 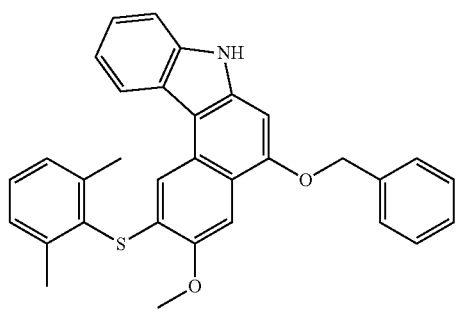 [SMILES: COc1cc2c(OCc3ccccc3)cc3[nH]c4ccccc4c3c2cc1Sc1c(C)cccc1C] | 92 |
[1] Yield corresponds to isolated phenylnaphthol intermediate cumulated from Steps 6-8;
[2] Yield corresponds to isolated indolenaphthol intermediate from Step 9.

Preparation of Examples 11 and 12

In the following examples, representative synthetic procedures for preparing indolenaphthpyran photochromic compounds are detailed. A scheme for the synthesis of Examples 11 and 12 is depicted below. "nBuI" refers to iodobutane, "DMF" refers to dimethylformamide, "pTSA" refers to para-toluenesulfonic acid, and "Ph" refers to phenyl. Each step of the synthesis is further described below.

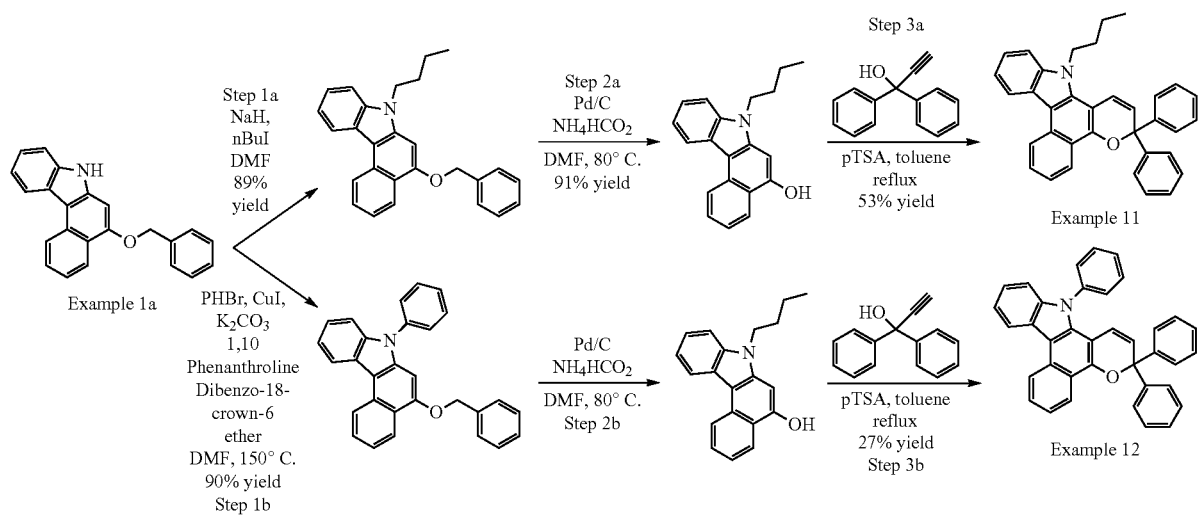

Example 11

Step 1a

While stirring under nitrogen, Example 1a (4.0 g, 12.4 mmol) was dissolved in anhydrous dimethylformamide (30 ml) and sodium hydride (0.9 g, 37.1 mmol) was added slowly. After 15 minutes, iodobutane (2.50 g, 13.6 mmol) was added and the reaction mixture was stirred at room temperature for 45 minutes. The reaction mixture was taken up in ethyl acetate (200 ml) and washed with water (3×200 ml). The organic layer was dried with sodium sulfate and concentrated under reduced pressure to give a brown solid. The solid was washed with methanol to yield an off-white powder (4.20 g, 89% yield).

Step 2a

While stirring under nitrogen, the product from Step 1 (4.0 g, 10.5 mmol) was combined with ammonium formate (2.75 g, 43.6 mmol) and palladium on carbon (Degussa type E1003 U/W, 0.37 g, 3.2 mmol) in dimethylformamide (100 ml). The reaction mixture was heated to 85° C. for 2 hours. Once cool, the reaction mixture was filtered over a pad of celite and the pad was washed with ethyl acetate (250 ml). The filtrate was washed with water (3×300 ml), dried with sodium sulfate and concentrated under reduced pressure to give a brown solid. The solid was precipitated into hexanes from dichloromethane to give an off-white powder (2.76 g, 91% yield).

Example 11

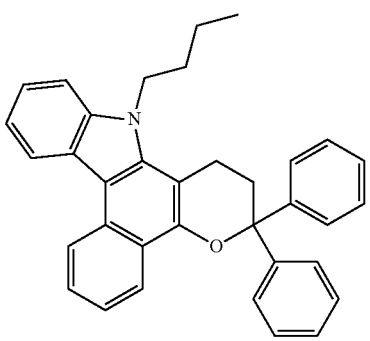

Step 3a

While stirring under nitrogen, the product from Step 2 (0.85 g, 2.90 mmol) was combined with 1,1-diphenylprop-2-yn-1-ol (0.73 g, 3.5 mmol) in toluene (25 ml) and heated towards reflux. p-Toluenesulfonic acid (5-10 mg) was added and the reaction mixture was heated to reflux for 1 hour. Once cool the reaction mixture was taken up in ethyl acetate (25 ml), washed with saturated sodium bicarbonate solution (25 ml) and water (2×50 ml). The organic layer was dried with sodium sulfate and concentrated under reduced pressure onto silica gel. Chromatography (silica gel, 0-25% dichloromethane in hexanes) yielded a dark oil. The product was recrystallized twice from methyl tert-butylether, tetrahydrofuran and methanol to give Example 11 as an off-white powder (0.73 g, 53% yield) and confirmed by mass spectrometry.

Example 12

Step 1b

While stirring under nitrogen, Example 1a (7.0 g, 21.6 mmol) was combined with bromobenzene (13.6 g, 86.4 mmol), copper iodide (2.06 g, 10.8 mmol), potassium carbonate (6.0 g, 43.2 mmol), 1,10-phenanthroline (0.78 g, 4.30 mmol) and dibenzo-18-crown-6-ether (0.80 g, 2.20 mmol) in anhydrous dimethylformamide (50 ml). The reaction mixture was heated to 150° C. for 4 hours. Once cool, the reaction mixture was taken up in ethyl acetate (250 ml) and washed initially with water (200 ml) with ethylene diamine (10 ml) followed by water (2×250 ml). The organic layer was dried with sodium sulfate and concentrated under reduced pressure onto silica gel. Chromatography (silica gel, 0-25% dichloromethane in hexanes) yielded a colorless powder that was washed with hexanes and dried under vacuum (7.82 g, 90% yield).

Step 2b

While stirring under nitrogen, the product from Step 1 (2.5 g, 6.26 mmol) was combined with ammonium formate (1.60 g, 25.0 mmol) and palladium on carbon (Degussa type E1003 U/W, 0.22 g, 1.9 mmol) in dimethylformamide (30 ml). The reaction mixture was heated to 80° C. for 2 hours. Once cool, the reaction mixture was filtered over a pad of celite and the pad was washed with ethyl acetate (250 ml). The filtrate was washed with water (3×300 ml), dried with sodium sulfate and concentrated under reduced pressure to give a brown oil used without further purification.

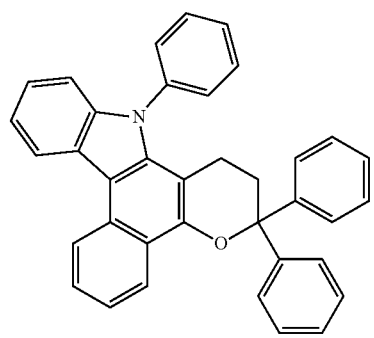

Example 12

Step 3b

While stirring under nitrogen, the product from Step 2 (0.50 g, 1.60 mmol) was combined with 1,1-diphenylprop-2-yn-1-ol (0.40 g, 2.0 mmol) in toluene (30 ml) and heated towards reflux. p-Toluenesulfonic acid (5-10 mg) was added and the reaction mixture was heated to reflux for 1 hour. Once cool, the reaction mixture was concentrated under reduced pressure onto silica gel. Chromatography (silica gel, 0-5% dichloromethane in hexanes) yielded a yellow solid. The product was recrystallized twice from dichloromethane and hexanes to give Example 12 as light yellow crystals (0.22 g, 27% yield) and confirmed by mass spectrometry.

The present invention can be further characterized by one or more of the following non-limiting clauses.

Clause 1. A phenylnaphthol compound, having the core skeletal structure represented by Formula (I):

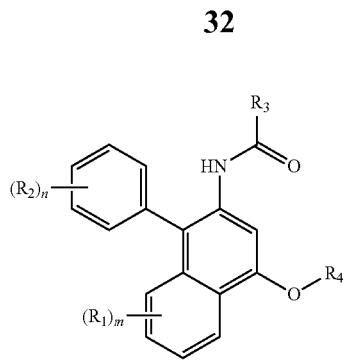

Formula (I)

wherein, m is 0 to 4;

n is 0 to 4;

$R^1$ and $R^2$ are each independently hydroxyl, cyano, (meth)acrylate, amino, halo, substituted or unsubstituted alkyl, boronic ester, boronic acid, polyether, polyester, polycarbonate, polyurethane, substituted or unsubstituted aryl, substituted or unsubstituted heterocycloalkyl, substituted or unsubstituted heteroaryl, substituted or unsubstituted alkoxy, substituted or unsubstituted aryloxy, substituted or unsubstituted alkylthio, substituted or unsubstituted arylthio, ketone, aldehyde, ester, carboxylic acid, carboxylate, amide, carbonate, carbamate, urea, siloxane, alkoxysilane, or polysiloxane;

wherein two $R^1$ groups or two $R^2$ groups on adjacent carbon atoms may connect to form a ring;

$R^3$ is selected from substituted or unsubstituted 2-pyridyl or substituted or unsubstituted 2-quinolyl;

wherein the pyridyl and quinolyl substituents are selected from substituted or unsubstituted alkyl, substituted or unsubstituted alkoxy, substituted or unsubstituted aryloxy, substituted or unsubstituted aryl, substituted or unsubstituted heteroaryl, halogen, amino, ester, carboxylate, or hydroxyl; and $R^4$ is selected from hydrogen, substituted or unsubstituted alkyl, alkoxymethyl, substituted or unsubstituted silyl, or acyl.

Clause 2. The phenylnaphthol compound of clause 1, wherein each alkyl substituent, each aryl substituent, each heterocycloalkyl substituent, each heteroaryl substituent, each alkoxy substituent, each aryloxy substituent, each alkylthio substituent, each arylthio substituent, and each silyl substituent is in each case independently selected from halogen, cyano, nitro, alkyl, alkenyl, alkynyl, haloalkyl, perhaloalkyl, heterocycloalkyl, aryl, heteroaryl, alkoxy, hydroxyl, alkylthio, arylthio, ketone, aldehyde, ester, carboxylic acid, carboxylate, siloxane, alkoxysilane, polysiloxane, amide, amine, carbamate, carbonate, urea, polyester group, polyether group, polycarbonate group, polyurethane group, an acrylate group, a (meth)acrylate group, aryl amine, alkyl amine, cyclic aminos, heteroaromatics, or combinations thereof.

Clause 3. The phenylnaphthol compound of clauses 1 or 2, wherein $R^1$ and $R^2$ are independently selected from a halo group, substituted or unsubstituted alkyl, substituted or unsubstituted heteroaryl, substituted or unsubstituted alkoxy, substituted or unsubstituted aryloxy, substituted or unsubstituted alkylthio, or substituted or unsubstituted arylthio.

Clause 4. The phenylnaphthol compound of clause 3, wherein $R^1$ or $R^2$ is alkoxy, alkyl, halo, trihaloalkyl, or arylthio.

Clause 5. The phenylnaphthol compound of clause 4, wherein $R^1$ or $R^2$ is methoxy, methyl, fluoro, trifluoromethyl, or arylthio.

Clause 6. The phenylnaphthol compound of clause 4, wherein $R^1$ or $R^2$ is alkoxy.

Clause 7. The phenylnaphthol compound of any of clauses 4 to 6, wherein $R^1$ or $R^2$ is methoxy.

Clause 8. The phenylnaphthol compound of any of clauses 1 to 4, wherein each halo group of $R^1$ or $R^2$ is selected from fluoro, chloro, bromo, or iodo.

Clause 9. The phenylnaphthol compound of any of clauses 1 to 8, wherein $R^3$ is 2-pyridyl.

Clause 10. The phenylnaphthol compound of any of clauses 1 to 9, wherein $R^4$ is benzyl.

Clause 11. The phenylnaphthol compound of any of clauses 1 to 10, wherein $R^1$ is at the positions depicted in the core skeletal structure of Formula (I') below:

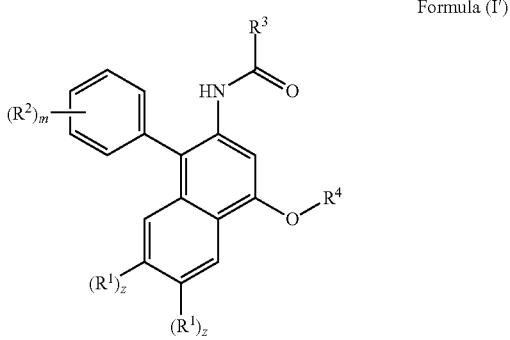

Formula (I')

wherein each z is independently 0 or 1.

Clause 12. The phenylnaphthol compound of any of clauses 1 to 11, wherein $R^2$ is at the position depicted in the core skeletal structure of Formula (I") below:

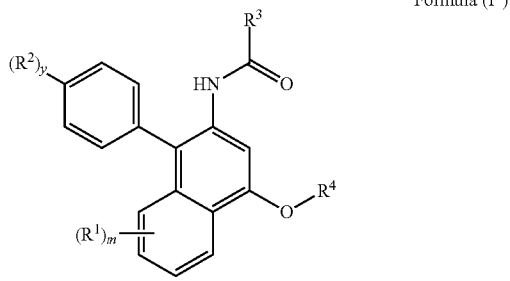

Formula (I")

wherein each y is independently 0 or 1.

Clause 13. A process for producing an indolenaphthol compound comprising the core skeletal structure represented by Formula (II):

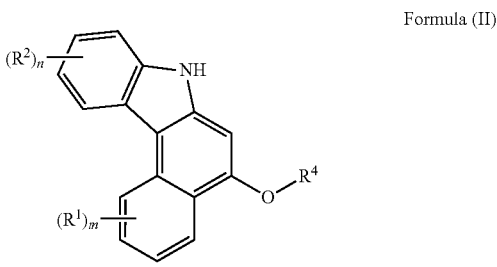

Formula (II)

wherein,
m is 0 to 4;
n is 0 to 4;
$R^1$ and $R^2$ are each independently hydroxyl, cyano, (meth)acrylate, amino, halo, substituted or unsubstituted alkyl, boronic ester, boronic acid, polyether, polyester, polycarbonate, polyurethane, substituted or unsubstituted aryl, substituted or unsubstituted heterocycloalkyl, substituted or unsubstituted heteroaryl, substituted or unsubstituted alkoxy, substituted or unsubstituted aryloxy, substituted or unsubstituted alkylthio, substituted or unsubstituted arylthio, ketone, aldehyde, ester, carboxylic acid, carboxylate, amide, carbonate, carbamate, urea, siloxane, alkoxysilane, or polysiloxane;
wherein two $R^1$ groups or two $R^2$ groups on adjacent carbon atoms may connect to form a ring;
$R^3$ is selected from substituted or unsubstituted 2-pyridyl or substituted or unsubstituted 2-quinolyl;
wherein the pyridyl and quinolyl substituents are selected from substituted or unsubstituted alkyl, substituted or unsubstituted alkoxy, substituted or unsubstituted aryloxy, substituted or unsubstituted aryl, substituted or unsubstituted heteroaryl, halogen, amino, ester, carboxylate, or hydroxyl; and
$R^4$ is selected from hydrogen, substituted or unsubstituted alkyl, alkoxymethyl, substituted or unsubstituted silyl, or acyl; and
the process comprises cyclizing the phenylnaphthol compound of any of clauses 1 to 12 in the presence of a catalyst.

Clause 14. The process of clause 13, wherein the catalyst is a transition metal catalyst.

Clause 15. The process of clauses 13 or 14, wherein the catalyst comprises copper, zinc, palladium, platinum, rhodium, or iridium.

Clause 16. The process of any of clauses 13 to 15, wherein the catalyst comprises copper.

Clause 17. The process of any of clauses 13 to 16, further comprising alkylating or arylating to produce an indolenaphthol compound comprising the core skeletal structure represented by Formula (III):

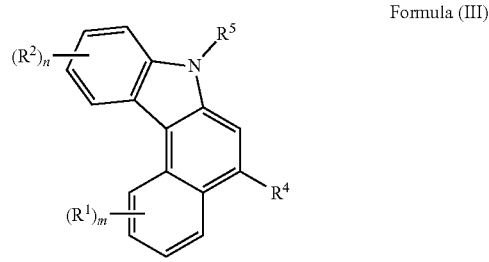

Formula (III)

wherein $R^5$ is selected from substituted or unsubstituted alkyl, substituted or unsubstituted aryl, or acyl.

Clause 18. The process of clause 17, wherein $R^5$ is alkyl.

Clause 19. The process of clauses 17 or 18, comprising alkylating by reaction with an alkyl halide, triflate, or tosylate in the presence of a base.

Clause 20. The process of clause 19, comprising deprotonating the indole with the base and reacting the resulting anion with the alkyl halide, triflate, or tosylate.

Clause 21. The process of clause 17, wherein $R^5$ is substituted or unsubstituted phenyl.

Clause 22. The process of clauses 17 or 21, comprising arylating by a cross coupling reaction with a transition metal catalyst and an aryl halide.

Clause 23. The process of clause 22, wherein the cross coupling reaction is an Ullmann coupling reaction with a copper catalyst.

Clause 24. The process of clauses 17 or 21, comprising arylating by nucleophilic aromatic substitution reaction with an aryl fluoride.

Clause 25. The process of any of clauses 13 to 24, further comprising deprotecting $R^4$ to generate a hydroxyl group, when $R^4$ is substituted or unsubstituted alkyl, alkoxymethyl, substituted or unsubstituted silyl, or acyl.

Clause 26. The process of clause 25, wherein deprotecting is carried out under palladium hydrogenation conditions or with a strong acid.

Clause 27. The process of clause 26, wherein deprotecting is carried out with palladium on carbon.

Clause 28. The process of any of clauses 13 to 27, further comprising reacting with a diaryl propargyl alcohol to form an indolenaphthopyran compound comprising a core skeletal structure represented by Formula (IV):

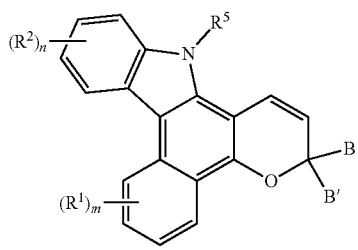

Formula (IV)

wherein B and B' are each independently substituted or unsubstituted aryl, or substituted or unsubstituted heteroaryl.

Clause 29. The process of clause 28, wherein reacting with a diaryl propargyl alcohol is carried out under acidic conditions.

Clause 30. The process of clauses 28 or 29, wherein B and B' are each independently substituted or unsubstituted phenyl.

Clause 31. The process of clause 30, wherein each phenyl substituent is in each case independently alkoxy, halo, alkyl, or aryloxy.

The present invention has been described with reference to specific details of particular embodiments thereof. It is not intended that such details be regarded as limitations upon the scope of the invention except insofar as to the extent that they are included in the accompanying claims.

What is claimed is:

1. A phenylnaphthol compound comprising the core skeletal structure represented by Formula (I):

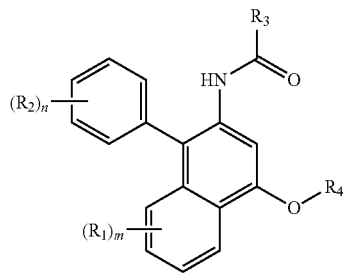

Formula (I)

wherein, m is 0 to 4, and n is 0 to 4;

$R^1$ independently for each m, and $R^2$ independently for each n, are each independently selected from:
i. a halo group selected from fluoro, chloro, bromo, or iodo;
ii. substituted or unsubstituted alkyl;
iii. substituted or unsubstituted heteroaryl;
iv. substituted or unsubstituted alkoxy or substituted or unsubstituted aryloxy;
v. substituted or unsubstituted alkylthio or substituted or unsubstituted arylthio;
or
two $R^1$ groups or two $R^2$ groups on adjacent carbon atoms may connect to form a ring;

$R^3$ is selected from substituted or unsubstituted 2-pyridyl or substituted or unsubstituted 2-quinolyl,
wherein the pyridyl or quinolyl substituents are selected from substituted or unsubstituted alkyl, substituted or unsubstituted alkoxy, substituted or unsubstituted aryloxy, substituted or unsubstituted aryl, substituted or unsubstituted heteroaryl, halogen, amino, ester, carboxylate, or hydroxyl; and $R^4$ is selected from hydrogen, substituted or unsubstituted alkyl, alkoxymethyl, substituted or unsubstituted silyl, or acyl.

2. The phenylnaphthol compound of claim 1, wherein each alkyl substituent, each aryl substituent, each heterocycloalkyl substituent, each heteroaryl substituent, each alkoxy substituent, each aryloxy substituent, each alkylthio substituent, each arylthio substituent, and each silyl substituent is in each case independently selected from halogen, cyano, nitro, alkyl, alkenyl, alkynyl, haloalkyl, perhaloalkyl, heterocycloalkyl, aryl, heteroaryl, alkoxy, hydroxyl, alkylthio, arylthio, ketone, aldehyde, ester, carboxylic acid, carboxylate, siloxane, alkoxysilane, polysiloxane, amide, amine, carbamate, carbonate, urea, polyester group, polyether group, polycarbonate group, polyurethane group, an acrylate group, a (meth)acrylate group, aryl amine, alkyl amine, cyclic aminos, heteroaromatics, or combinations thereof.

3. The phenylnaphthol compound of claim 1, wherein $R^1$ or $R^2$ is alkoxy.

4. The phenylnaphthol compound of claim 1, wherein $R^3$ is 2-pyridyl.

5. The phenylnaphthol compound of claim 1, wherein $R^4$ is benzyl.

6. A process for producing an indolenaphthol compound comprising:
(1) providing a phenylnaphthol compound comprising the core skeletal structure represented by Formula (I):

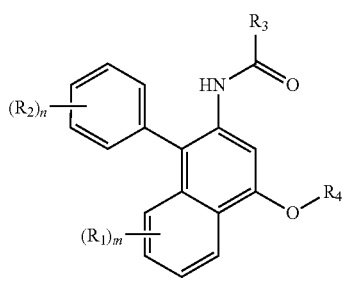

Formula (I)

wherein,
m is 0 to 4, and n is 0 to 4;
$R^1$ independently for each m, and $R^2$ independently for each n, are each independently selected from:
i. a halo group selected from fluoro, chloro, bromo, or iodo;
ii. substituted or unsubstituted alkyl;
iii. substituted or unsubstituted heteroaryl;
iv. substituted or unsubstituted alkoxy or substituted or unsubstituted aryloxy;
v. substituted or unsubstituted alkylthio or substituted or unsubstituted arylthio; or
two $R^1$ groups or two $R^2$ groups on adjacent carbon atoms may connect to form a ring;
$R^3$ is selected from substituted or unsubstituted 2-pyridyl or substituted or unsubstituted 2-quinolyl, wherein the pyridyl or quinolyl substituents are selected from substituted or unsubstituted alkyl, substituted or unsubstituted alkoxy, substituted or unsubstituted aryloxy, substituted or unsubstituted aryl, substituted or unsubstituted heteroaryl, halogen, amino, ester, carboxylate, or hydroxyl; and
$R^4$ is selected from hydrogen, substituted or unsubstituted alkyl, alkoxymethyl, substituted or unsubstituted silyl, or acyl; and
(2) cyclizing the phenylnaphthol compound of Formula (I) in the presence of a transition metal catalyst to produce an indolenaphthol compound having the core skeletal structure represented by Formula (II):

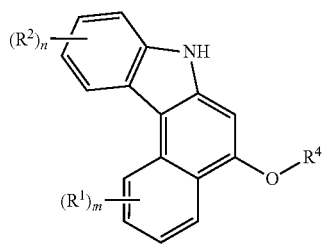

Formula (II)

wherein m, n, $R^1$, $R^2$, and $R^4$ are as defined above by Formula (I).

7. The process of claim 6, further comprising alkylating or arylating to produce an indolenaphthol compound comprising the core skeletal structure represented by Formula (III):

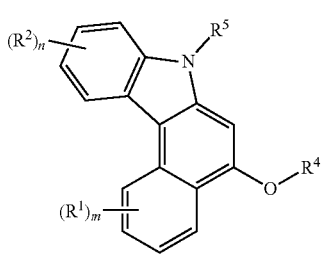

Formula (III)

wherein $R^5$ is selected from substituted or unsubstituted alkyl, substituted or unsubstituted aryl, or acyl.

8. The process of claim 7, further comprising:
deprotecting $R^4$ to generate a hydroxyl group, when $R^4$ is substituted or unsubstituted alkyl, alkoxymethyl, substituted or unsubstituted silyl, or acyl, and
reacting with a diaryl propargyl alcohol to form an indolenaphthopyran compound comprising a core skeletal structure represented by Formula (IV):

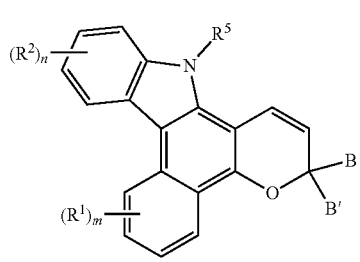

Formula (IV)

wherein B and B' are each independently substituted or unsubstituted aryl, or substituted or unsubstituted heteroaryl.

9. The process of claim 6, wherein the transition metal catalyst comprises copper, zinc, palladium, platinum, rhodium, or iridium.

10. The process of claim 9, wherein the catalyst comprises copper.

11. The process of claim 7, comprising alkylating by reaction with an alkyl halide, triflate, or tosylate in the presence of a base.

12. The process of claim 7, comprising arylating by a cross coupling reaction with a transition metal catalyst and an aryl halide.

* * * * *